United States Patent
Tham et al.

[11] Patent Number: 6,068,602
[45] Date of Patent: May 30, 2000

[54] METHOD AND APPARATUS FOR DETERMINING AIRWAY RESISTANCE AND LUNG COMPLIANCE

[75] Inventors: Robert Q. Tham; Duncan P. L. Bathe; William M. Theisen, all of Madison, Wis.

[73] Assignee: Ohmeda Inc., Liberty Corner, N.J.

[21] Appl. No.: 08/938,162

[22] Filed: Sep. 26, 1997

[51] Int. Cl.[7] .......................................... A61B 5/00
[52] U.S. Cl. ........................... 600/533; 600/529; 600/538
[58] Field of Search ..................................... 600/529, 533, 600/538

[56] References Cited

U.S. PATENT DOCUMENTS

| | | | |
|---|---|---|---|
| 5,316,009 | 5/1994 | Yamada | 600/533 |
| 5,318,038 | 6/1994 | Jackson et al. | |
| 5,522,397 | 6/1996 | Vermaak | 600/533 |
| 5,680,871 | 10/1997 | Ganshorn | 600/533 |
| 5,752,921 | 5/1998 | Orr | 600/533 |

OTHER PUBLICATIONS

Partitioning of Lung Tissue Response and Inhomogeneous Airway Constriction at the Airway Opening, Journal of Applied Physiology, vol. 82, No. 4, Apr. 1997, pp. 1349–1350, XP002087895.

*Primary Examiner*—Robert L. Nasser
*Attorney, Agent, or Firm*—Andrus, Sceales, Starke & Sawall

[57] ABSTRACT

A method and apparatus is disclosed for determining airway resistance and lung compliance using an electrical circuit model wherein at least one component parameter is non-linear. The system non-intrusively obtains pressure and flow data signals from a pressure transducer and a laminar flow element without interrupting or interfering with normal breathing and gas supply to a patient. An invariant exponential is determined empirically based on physical characteristics of the airway. The non-linear airway resistance and lung compliance can then be calculated based on the sensed flow rate, gas pressure, a calculated gas volume, and the invariant exponential using linear techniques. The resulting airway resistance can be normalized to a standard reporting flow rate value. The system is particularly useful in anesthesia applications, but is also useful in any breathing system where fresh gas is supplied constantly from a gas source other than a ventilator.

19 Claims, 3 Drawing Sheets

METHOD AND APPARATUS FOR DETERMINING AIRWAY RESISTANCE AND LUNG COMPLIANCE

BACKGROUND OF THE INVENTION

The present invention relates generally to determining airway resistance and lung compliance, and more particularly to using a circuit model approach to find the airway resistance and lung compliance where at least one component is non-linear.

In an anesthesia procedure, it is advantageous to know with some certainty the airway resistance and lung compliance in order to ascertain the suitability of the ventilatory management system. Although many attempts have been made to determine airway resistance, most assume the resistance to be linear, when in fact, it is not. Others do not consider the effects of lung compliance. Therefore, both types of systems fall far short of determining either parameter with any certainty and in some cases, results in gross inaccuracies.

It will be shown herein that those systems that assume a linear resistance relationship between pressure and flow in the patient airway will not function properly on intubulated patients. It is also believed that since an endotracheal tube follows the natural path and shape of a patient's airway, such linear systems will not function properly if applied directly to the patient's airway passage. The error found in the results from such linear techniques for determining resistance and compliance will increase dramatically with varying ventilation flow rates. Changing flow rates is common in anesthesia procedures and can be caused by changes to ventilatory settings of tidal volumes, inspiratory flows, or fresh gas delivery to the breathing circuit. In order to assume such a linear relationship then, one must maintain a constant flow rate. However, such an undesirable dependence on requiring a constant flow rate, can also impose errors to the very parameters being estimated because flow rate changes during each breath cycle as well.

Some prior art systems require the injection of an excitation flow into the breathing circuit or an inspiratory pause in order to calculate the airway resistance and lung compliance. However, such techniques are not practical during an anesthesia procedure. In fact, in any breathing system where fresh gas is supplied constantly from a gas source other than the ventilator, an inspiratory pause cannot be imposed.

Other known systems use a forced high frequency oscillation to determine airway resistance and lung compliance. The problem with this system is that no one good resonant frequency can be determined for all patients. Attempting to find the correct frequency for each patient would be time consuming and not practical.

One early attempt at determining lung airway resistance non-linearly is disclosed in U.S. Pat. No. 3,036,569. However, merely finding a resistance at one flow rate does not provide sufficient data to be useful in anesthesia procedures. It has also been found that pressure is not a function of resistance only, but also of compliance. Further, this reference requires an apparatus that forces air into the lung in order to perform the calculation, which would interfere with normal breathing and with anesthesia flow.

It would therefore be desirable to have a system, including a method and apparatus, that does not interfere with normal breathing, is non-intrusive with the normal flow and pressure during an anesthesia procedure, can measure pressure and flow on expiration, does not interrupt or interfere in any way with the respiratory pattern, and can find both airway resistance and lung compliance, while still reporting the non-linear air resistance at a standardized flow rate.

SUMMARY OF THE INVENTION

The present invention provides a system for determining the non-linear airway resistance and lung compliance using a circuit model approach that overcomes the aforementioned problems.

In accordance with one aspect of the invention, a non-linear method of establishing airway resistance and lung compliance is disclosed using a circuit model. The method includes the steps of sensing a gas flow rate through an airway and sensing a gas pressure in the airway, then calculating a gas volume from the gas flow rate, and determining an invariant exponential based on physical characteristics of the airway. Airway resistance and lung compliance can then be accurately calculated based on the gas flow rate, the gas pressure, the gas volume, and the invariant exponential at any flow rate.

In accordance with another aspect of the invention, an apparatus is disclosed to determine airway resistance and lung compliance. The apparatus includes an airway capable of communicating external gas with a patient's lungs, a gas flow rate sensor attached to the airway to sense a gas flow through the airway and produce a flow signal in response, and a gas pressure sensor located in the airway to sense a gas pressure across the airway and produce a pressure signal in response. A processor, such as a computer, a central processing unit, a microcontroller, or any other type of processing unit, is connected to the gas flow and pressure sensors to receive the flow and pressure signals. The processor is programmed to calculate airway resistance and lung compliance using a non-linear model having at least one non-linear component.

The current system does not require injection of excitation flows into the breathing circuit or an inspiratory pause to calculate the airway resistance and lung compliance, as required in the prior art. The present invention acquires pressure and gas flow rate signals from pressure transducers which measure the relative airway pressure and the pressure across a laminar flow element without interruption or interference with normal gas flow.

The analog signals acquired are digitized and supplied to a processor which is programmed to calculate the non-linear airway resistance and lung compliance according to an electrical circuit model. The total airway pressure is equal to the sum of the pressure due to the flow rate, the pressure due to the volume, a pressure constant, and the pressure due to flow change, which in most cases is minimal and can be ignored. The pressure due to flow rate, or resistance, is empirically determined to be non-linear. Various airways such as endotracheal tubes are analyzed and are fit to a common equation in order to determine an invariant exponential. Data is acquired at three convenient points along the expiration cycle in order to solve the circuit model equation by common linear algebra techniques. The resistance can then be converted to a standardized reporting flow rate. Such conversion however is optional since the resistance calculated is accurate at any flow rate, unlike linear resistance models.

Various other features, objects, and advantages of the present invention will be made apparent from the following detailed description and the drawings.

BRIEF DESCRIPTION OF THE DRAWING

The drawings illustrate the best mode presently contemplated for carrying out the invention.

In the drawings.

DETAILED DESCRIPTION OF THE PREFERRED EMBODIMENT

Figure 1:
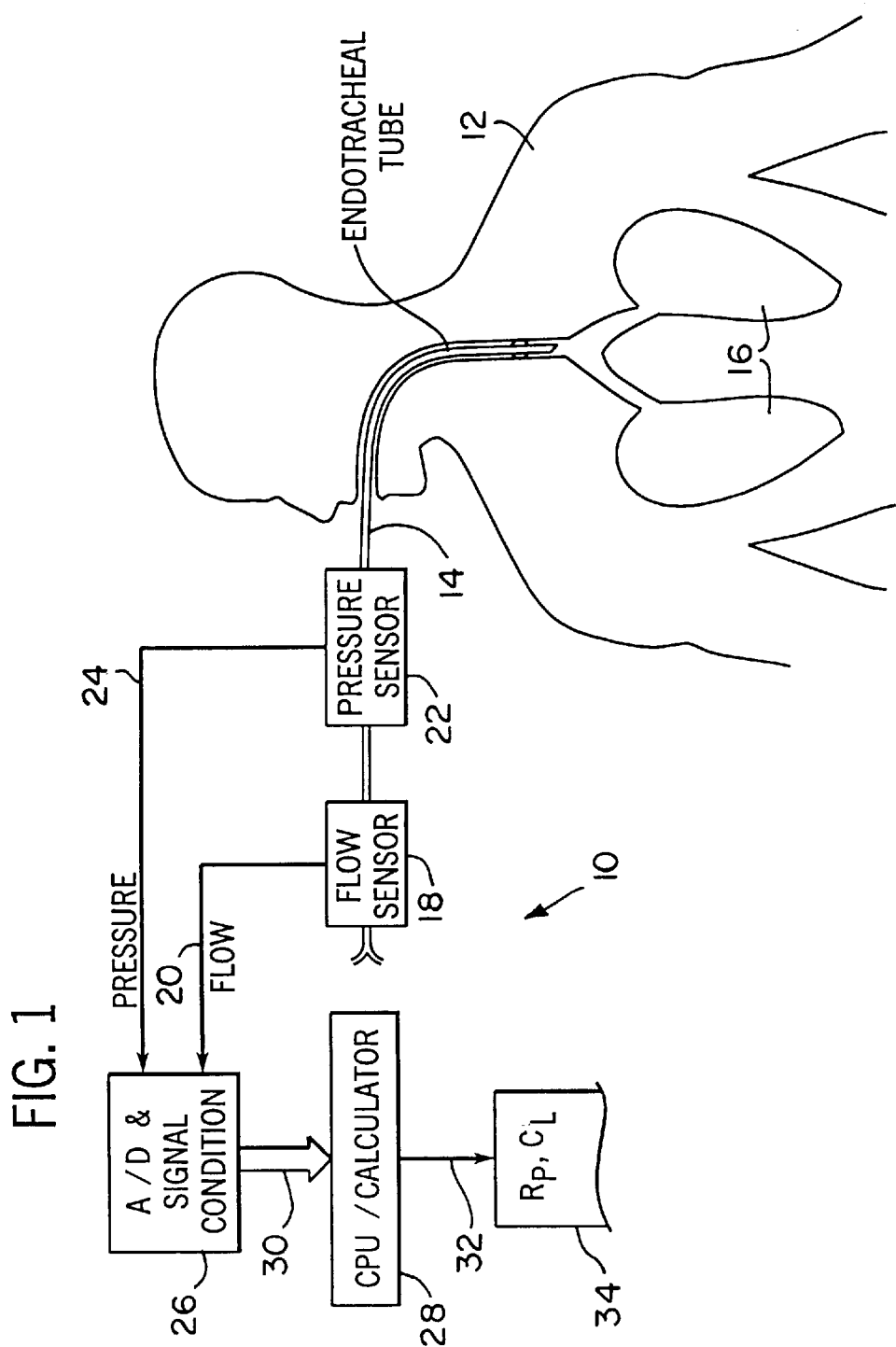
FIG. 1 shows a block diagram of a system in accordance with the present invention as applied to a human subject.

FIG. 1 shows a system 10 which includes an apparatus to determine airway resistance and lung compliance in a patient 12. In one application of the present invention, an endotracheal tube 14 acts as an airway between an external oxygen source (not shown), which can include an anesthesia component, and the lungs 16 of patient 12. The system 10 includes a gas flow rate sensor 18 attached to the airway 14 to sense a gas flow therethrough and produce a flow signal 20. A gas pressure sensor 22 is also located in airway 14 to sense a gas pressure therein and produce a pressure signal 24 from the sensed gas pressure in airway 14. The flow and pressure signals 20, 24 may be provided by pressure transducers in the flow sensor 18 and the pressure sensor 22 which measure the relative pressure across a laminar flow element and the relative airway pressure, respectfully. The signals 20, 24 are proportional to the pressure and flow and are filtered to remove noise and errant signals by the A/D and signal conditioner 26, which also converts the analog signals to digital form for processing by a CPU 28. The data acquisition occurs on a discrete time basis; that is, the A/D converter 26 establishes a data value for the respective signal over its sampling interval, later referred to as the sampling time.

The CPU 28 is connected to the gas flow sensor 18 and the pressure sensor 22 via the A/D converter 26 to receive digitized flow and pressure signals 30. The CPU 28 is programmed to calculate the airway resistance $R_P$ and the lung compliance $C_L$ using a non-linear circuit model having at least one non-linear component, as will be further described with reference to FIGS. 2–4. Once the airway resistance $R_P$ and the lung compliance $C_L$ are known, representative signals 32 can be transmitted to an external monitoring apparatus 34 to monitor the ventilatory management system. Although FIG. 1 shows the system 10 of the present invention applied to an airway in the form of an endotracheal tube 14, the present invention is not so limited. For example, the patient may be fitted with a mask having an external airway 14 attached thereto.

Figure 2:
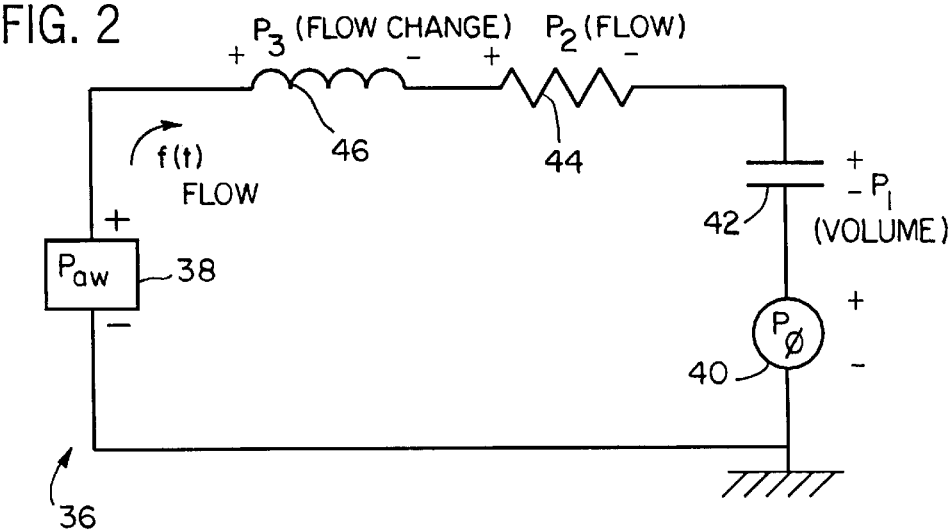
FIG. 2 is a circuit schematic of the circuit modeling approach encompassed in the system of FIG. 1.

Referring to FIG. 2, a circuit schematic 36 is used to illustrate the circuit model approach used to determine the airway resistance $R_P$ and the lung compliance $C_L$ according to the present invention. To more accurately find the airway resistance $R_P$ and the lung compliance $C_L$, the mechanics of the respiratory system are approximated by a mathematical model that relates airway pressure $P_{aw}$ at the vicinity of the patient's mouth to the bidirectional gas flow in and out of the lungs. This mathematical model is illustrated as the circuit model of FIG. 2. The functional relationship is described as:

$$P_{aw} = P0 + P1(\text{volume}) + P2(\text{flow}) + P3(\text{flow changes}) \quad (1)$$

Figure 3:
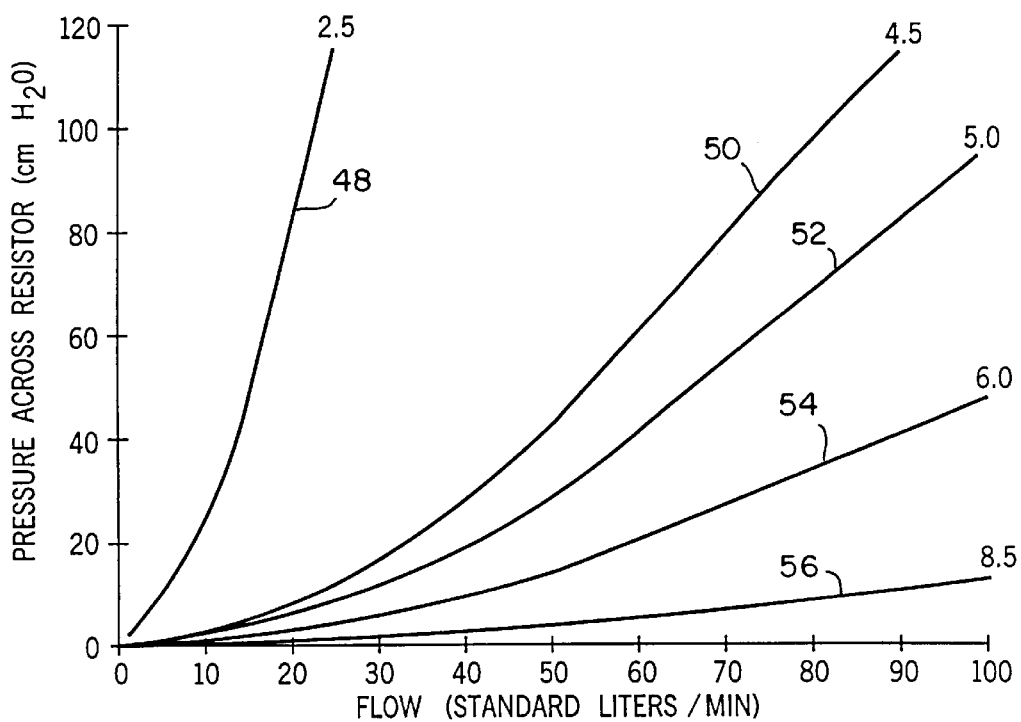
FIG. 3 is a graph showing flow versus pressure across the resistor for various airway tubes.

Each of the Px terms on the right side of Equation (1) are various pressure contributions from the pulmonary system to the total airway pressure $P_{aw}$ 38. P0 is a constant related to volume offset, end-expiratory pressure, gravitational effects, etc., and is therefore represented as a constant voltage source 40. P1 is a function of volume and is related to the lung compliance effects, and therefore appropriately represented as capacitor 42. The airway restriction P2 is modeled as a resistor 44, however, as will be described with reference to FIG. 3, is a non-linear function of flow. P3 is the chestwall and gas inertia effects which can be represented by inductor 46. The circuit model 36 of FIG. 2 and Equation 1 are based on the well known Kirchhoff's voltage law which states that the algebraic sum of the voltages around any closed path is zero. This law applies equally to the pressures in the pulmonary system.

While it is arguable whether the inertia component P3 is required in the model at all, it has been found that it is only significant at respiratory rates higher than 66 breaths per minutes (bpm). In anesthesia procedures, respiratory rates are typically 40 bpm or less, and therefore the inertia component relating pressure to changes in respiratory flow rates is insignificant and can be ignored. However, for other purposes, one skilled in the art will readily recognize that the inertia effects P3 can be incorporated into the calculations, if desired, in accordance with the present invention.

In an anesthesia procedure, the functional relationship of the restriction term P2, indicated by resistor 44, is dominated by the flow-through resistance in the endotracheal tube 14, FIG. 1. With the exception of late expiration, it is known that gas flow through an endotracheal tube is turbulent. FIG. 3 shows the relationship between pressure in an endotracheal tube on the y-axis, and gas flow through the tube on the x-axis. The various curves show that the pressure versus gas flow relationship (resistance) is clearly non-linear. Each of the curves depict the results from a different sized endotracheal tube. Curve 48 shows the relationship between pressure and flow for a 2.5 mm. endotracheal tube, curve 50 shows the pressure/flow relationship for a 4.5 mm. tube, curve 52 shows the relationship for a 5.0 mm. tube, curve 54 shows that relationship for a 6.0 mm. tube, and curve 56 shows the non-linear properties for a 8.5 mm. tube. The data presented in FIG. 3 can be used to find a common exponential such that each curve can be approximated by a common equation. Using common techniques, this pressure/flow relationship can be approximated by an exponential function, as shown in Equation 2, or a polynomial series, as shown in Equation 3.

$$P2(F) = K1 * f(t)^n \quad (2)$$

$$P2(F) = A0 = A1 * f(t) + A2 * f(t)^2 + \ldots \quad (3)$$

In a typical ventilatory range during anesthesia, the parameters K1 and the Ax terms remain constant within any single breath. The f(t) term is the instantaneous bidirectional flow rate. From the graph in FIG. 3, the data for the pressure and flow can then be used to find the unknown exponential n. For the various endotracheal tubes shown in FIG. 3, it has been found that an invariant exponential value of 1.7 fits each of these curves.

It has also been found that within any single breath, the pressure contribution of the compliance term P1 is proportional to the volume in the lung. The pressure due to volume extension in the lungs acts like an electrically charged capacitor in that increasing the volume in the lung, increases the pressure. According to the present invention, the following equation is used to model and calculate patient pulmonary mechanics:

$$P_{aw} = L + 1/C_L * v(t) + K_p * f(t)^n \quad (4)$$

Equation 4 is the particular equation that relates to the general Equation 1 with the insignificant inertia term P3 assumed to be zero. The L term is the P0 constant term. $C_L$ is modeled as the compliance of the lung and v(t) is the instantaneous volume in the lung. The lung volume v(t) is found by integrating the bidirectional flow rate, as will be described in more detail with reference to FIG. 4. The product of the inverse lung compliance and the volume is the P1 volume term in Equation 1. The $K_P$ term is a constant that relates the exponential flow rate to the pressure difference contributed by the airway restriction, and changes for each airway tube. Again, f(t) is the bidirectional flow, and n is the empirically determined invariant exponential determined a priori. The product of the flow and the $K_P$ constant for each tube corresponds to the P2 flow term in Equation 1, and is the pressure due to the flow across the resistor.

The curves of FIG. 3 were plotted by placing a constant gas flow through each tube and measuring the flow rate output as well as the change in pressure across the tube. The invariant exponential is found by fitting each curve to a common function and although the $K_P$ term changes for each tube, or resistor, the exponential remains the same. In this case, and it is presumed for all tubular airways, the invariant exponential is 1.7 which represents the curvature in the endotracheal tube. It is understood that different geometries of airway configurations may change the invariant exponential. However, during anesthesia, the endotracheal tube dominates the airway resistance. These tubes are similar to the those used empirically to derive the exponent. In masked cases where patients are not intubated, the trachea is the dominant airway resistance. Consequently, the invariant exponent value of 1.7 applies to most anesthesia cases.

As will now be evident, having a value for the exponent, and measurements for the bidirectional flow rate, f(t), the airway pressure, $P_{aw}$, and a calculated volume, v(t), the calculation of the airway resistance, $R_P$, and the lung compliance, $C_L$, is reduced to a problem of value identification for $C_L$ and $K_P$, and ultimately, the linear airway resistance $R_P$. In the preferred embodiment, the solution presented uses simultaneous equations of three sets of data points to solve for the unknown $C_L$ and $K_P$. Specifically, three convenient points are chosen to obtain data. The first is at a time $T_1$ when the flow rate is equal to zero at the beginning of an expiration. The second is at a time $T_2$ when the flow rate is at a maximum negative flow rate after time $T_1$, and the third is at a time $T_3$ after $T_2$ when the flow rate is 50% of the maximum negative flow rate. In other words, the three sets of data points are taken at the end of inspiration, at maximum negative expiratory flow and at 50% expiratory flow.

In this case, expiration, or flow out of the patient, is chosen negative. The equations and the data points may then be represented in matrix notation and may be solved by various known techniques. For example, a basic matrix augmentation and row reduction approach can be used for simplicity. However, one skilled in the art will recognize that various other techniques can be implemented to solve for the unknown lung compliance $C_L$ and the non-linear airway resistance $K_P$, such as regression or digital filtering. Such methods are less sensitive to measurement noises but are computationally intensive.

In practice, users are familiar and comfortable with a resistance representation, $R_P$, that linearly relates airway pressure and flow rate. To meet this expectation, all the non-linear airway resistances are mapped to linear resistances referenced at a standardized gas flow rate before it is reported. This linear airway resistance varies with flow rate and should only be compared at the referenced flow rate. The following relationship is used to report the airway resistance at a referenced flow rate:

$$R_P = K_P * F_{ref}^{n-1} \quad (5)$$

where $R_P$ is the linear airway resistance at a referenced flow rate $F_{ref}$. In practice, it is convenient to report the airway resistance at a standardized 30 liters per minute flow rate.

Although the preferred embodiment describes the aforementioned relationships for an anesthesia application, the present invention is readily applicable to other ventilatory conditions or environments wherein the terms contributing to airway pressure can be described by different relationships or constants.

Figure 4:
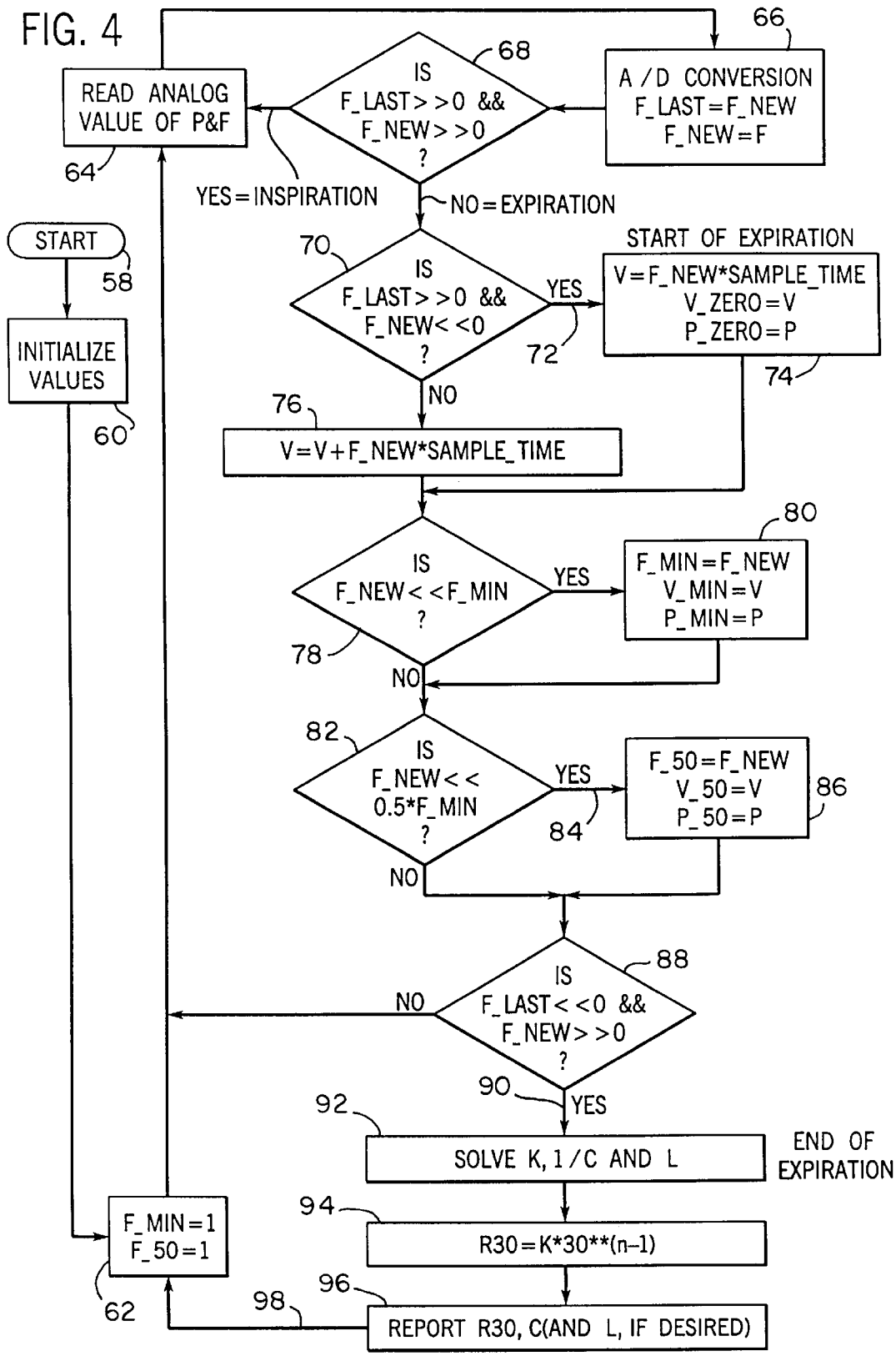
FIG. 4 is a flow chart used in implementing the system of FIG. 1.

Referring to FIG. 4, the software algorithm is described in flow chart form. The flow chart of FIG. 4 includes data acquisition at three points during expiration, volume determination, calculation of the unknowns, and conversion of the airway resistance to a standardized flow rate. Upon start up 58 all values are initialized to "1" 60 and 62. The analog values for the pressure and flow are read 64 from the pressure and flow sensors and the analog signals are then digitized 66. The flow and pressure values at the minimum flow (F_ZERO) are determined by continuously monitoring the present and previous flow rates to differentiate between inspiration and expiration 68, 70. When the present flow (F_NEW) is zero or less than zero, and the previous flow (F_LAST) is above zero, then the minimum flow (F_MIN) has been found 72, indicating the beginning of an expiration cycle in which the values for flow and pressure can be determined and saved as the minimum flow values (V_ZERO, P_ZERO) 74. If the present flow (F_NEW) is at zero, then the flow, volume, and pressure values are simply saved. However, if the present flow is less than zero, then the values are interpolated for zero flow and the interpolated values are saved for V_ZERO and P_ZERO. Once an expiration cycle has commenced and zero flow has not yet been reached, the volume value is updated 76 by adding the previous value for the volume to the product of the latest flow value and its respective sampling time.

Next, a maximum negative flow determination is made. After the zero flow value has been found, the system continuously monitors the flow signal to determine when it has reached a maximum negative value 78. This is accomplished by continuously comparing the present flow value (F_NEW) with the previously saved value (F_MIN). When the present value is less than the previous value, then the negative value is set to this present value at 80 and the volume and pressure for this flow rate value are saved as V_MIN and P_MIN. Again, in determining these values it has earlier been assumed that the flow rate out of the patient is negative. The flow rate could be assumed positive, with corresponding changes in the previous terminology.

The last data points are determined at a 50% flow rate. To find F_50, the system continuously monitors the flow signal to determine when it reaches 50% of the previously found maximum negative flow rate value (F_MIN). This is accomplished by comparing the present flow value (F_NEW) with 50% of the maximum negative flow value (F_MIN) at 82. When the present value is less than half the value 84, the volume and pressure related to this 50% flow rate value are stored as V_50 and P_50 86.

At the end of an expiration cycle 88, 90, the unknowns $K_P$, $C_L$ and L can be found at 92, as previously set forth. The resistance is then standardized 94 and can be reported to an external monitoring apparatus 96 and the system can then reiterate 98.

In practice, gases may be lost from the lung thereby making the lung volume actually smaller than the integrated bidirectional flow. The total volume loss within a breath can be determined by the difference of the inspired tidal volume to the expired tidal volume. The instantaneous volume losses may be estimated by apportioning the ratio of the total volume loss in that breath to the instant of volume measurement. The ratio would be determined empirically. This would then minimize the affect of volume loss in the resistance and compliance calculation of the present invention.

Accordingly, the present invention also includes a non-linear method of establishing airway resistance and lung compliance using a circuit model. The method includes the steps of sensing gas flow rate through an airway and sensing gas pressure in the airway. The method also includes calculating a gas volume from the gas flow rate and determining an invariant exponential based on the physical characteristics of the airway. Airway resistance and lung compliance can then be calculated based on the gas flow rate, the gas pressure, the gas volume, and the invariant exponential, as previously set forth.

As described with reference to FIG. 4, the step of calculating gas volume includes differentiating between expiration and inspiration flow rates and multiplying each sensed expiration gas flow rate by a corresponding sampling time for a current gas volume sample. The results are then integrated as a series of current gas volume samples during the expiration cycle. After at least three sets of data are acquired, the airway resistance and lung compliance can be calculated by either forming a matrix of the acquired data and solving the matrix, or with the use of regressive techniques that are commonly known.

The present invention has been described in terms of the preferred embodiment, and it is recognized that equivalents, alternatives, and modifications, aside from those expressly stated, are possible and within the scope of the appending claims.

We claim:

1. A method of establishing the airway resistance and lung compliance of a subject using a non-linear circuit model, the subject inspiring and expiring breathing gases through an airway, said method comprising the steps of:

sensing breathing gas flow rate through the airway;

sensing breathing gas pressure in the airway;

calculating a gas volume moved through the airway from the sensed breathing gas flow rate;

determining an invariant exponential based on physical characteristics of the airway; and calculating airway resistance and lung compliance based on the gas flow rate, the gas pressure, the gas volume, and the invariant exponential.

2. The method of claim 1 wherein the step of sensing gas flow rate and pressure are further defined as sensing the breathing gas flow rate and pressure in an airway having an endotracheal tube.

3. The method of claim 1 wherein the step of calculating gas volume further comprises the steps of:

differentiating between expiration and inspiration flow;

multiplying each sensed expiration gas flow rate by a corresponding sampling time to obtain a current gas volume sample; and integrating a series of current gas volume samples during an expiration cycle to obtain the calculated gas volume.

4. The method of claim 1 further comprising the steps of:

acquiring at least three sets of data from the sensing steps; and forming a matrix of the acquired data for calculating the airway resistance and lung compliance.

5. The method of claim 1 further comprising the steps of:

acquiring at least three sets of data from the sensing steps; and regressively calculating the airway resistance and lung compliance using the acquired data.

6. The method of claim 1, wherein the airway is tubular and the invariant exponential is determined at approximately 1.7.

7. The method of claim 1 wherein the step of calculating airway resistance and lung compliance is further defined as solving the equation:

$$P_{aw} = L + 1/C_L * v(t) + K_P * f(t)^n$$

where $P_{aw}$ is the sensed airway pressure, $v(t)$ is the calculated airway volume, $f(t)$ is the flow rate, n is the invariant exponential, L is a constant term, $C_L$ is the lung compliance, and $K_P$ is the airway resistance.

8. The method of claim 7 wherein the airway resistance is normalized to a standard flow rate given by:

$$R_P = K_P * F_{ref}^{n-1}$$

where $F_{ref}^{n-1}$ is a referenced flow rate and $R_P$ is the normalized airway resistance.

9. The method of claim 1 wherein the step of determining an invariant exponential is dependent on a shape and size of the airway and is determined empirically.

10. An apparatus to determine the airway resistance and lung compliance of a subject using a non-linear circuit model, the subject inspiring and expiring breathing gases through an airway, said apparatus comprising:

a breathing gas flow rate sensor attachable to the airway to sense a gas flow therethrough and produce a flow rate signal therefrom;

a breathing gas pressure sensor locatable in the airway to sense a gas pressure therein and produce a pressure signal therefrom; and a processor connected to the gas flow and pressure sensors to receive the flow and pressure signals, the processor calculating a gas volume moved through the airway and employing an invariant exponential based on the physical characteristics of the airway to calculate airway resistance and lung compliance using the gas flow rate, the gas pressure, the gas volume, and the invariant exponential.

11. The apparatus of claim 10, wherein the airway is tubular shaped and the invariant exponential is approximately 1.7.

12. The apparatus of claim 10 wherein the processor carries out the airway resistance and lung compliance calculation using the equation:

$$P_{aw} = L + 1/C_L * v(t) + K_P * f(t)^{n-1}$$

where $P_{aw}$ is the sensed airway pressure, $v(t)$ is the calculated airway volume, $f(t)$ is the flow rate, n is the invariant exponential, L is a constant term, $C_L$ is the lung compliance, and $K_P$ is the airway resistance.

13. The apparatus of claim 12 wherein the airway resistance is normalized to a standard flow rate given by:

$$R_P = K_P * F_{ref}^{n-1}$$

where $F_{ref}^{n-1}$ is a referenced flow rate and $R_P$ is the normalized airway resistance.

14. The apparatus of claim 10 further comprising:

a signal conditioner to filter errant and noise signals received from the sensors; and an A/D converter connected to receive analog signals from the gas flow rate sensor and the gas pressure sensor and produce digital signals in response.

15. The apparatus of claim 10 wherein the processor initially calculates a gas volume from the received flow rate signals.

16. The apparatus of claim 10 wherein the processor calculates the gas volume by:

differentiating between expiration and inspiration breathing gas flow;

multiplying each sensed expiration gas flow rate by a corresponding sampling time to obtain a current gas volume sample; and integrating a series of current gas volume samples during an expiration cycle to obtain the calculated gas volume.

17. The apparatus of claim 10 wherein the airway is an endotracheal tube.

18. The apparatus according to claim 10 wherein said processor is further defined as calculating airway resistance and lung compliance using at least three sets of data and forming a matrix of the data.

19. The apparatus of claim 10 wherein said processor is further defined as calculating airway resistance and lung compliance using at least three sets of data and regressively calculating the airway resistance and lung compliance using the data.

* * * * *